United States Patent [19]

Shen

[11] 3,954,792
[45] May 4, 1976

[54] 2-DIALKYLAMINO-5-TRIFLUOROMETHYL-7-NITROBENZIMIDAZOLES

[75] Inventor: Kelvin Kei-Wei Shen, Fountain Valley, Calif.

[73] Assignee: United States Borax & Chemical Corporation, Los Angeles, Calif.

[22] Filed: Mar. 6, 1975

[21] Appl. No.: 556,076

[52] U.S. Cl. .................. 260/309.2; 71/92
[51] Int. Cl.² ................... C07D 235/30
[58] Field of Search .................. 260/309.2

[56] References Cited
UNITED STATES PATENTS

| | | | |
|---|---|---|---|
| 3,325,271 | 6/1967 | Goldsmith et al. | 260/309.2 |
| 3,401,174 | 9/1968 | Woods et al. | 260/309.2 |
| 3,515,866 | 6/1970 | Goldsmith et al. | 260/309.2 |
| 3,528,798 | 9/1970 | Koloman | 260/309.2 |
| 3,655,901 | 4/1972 | Jensen et al. | 260/309.2 |
| 3,755,346 | 8/1973 | Soper | 260/309.2 |

FOREIGN PATENTS OR APPLICATIONS

| | | | |
|---|---|---|---|
| 1,430,139 | 1/1966 | France | 260/309.2 |
| 632,578 | 11/1963 | Belgium | 260/309 |

*Primary Examiner*—Natalie Trousof
*Attorney, Agent, or Firm*—James R. Thornton

[57] ABSTRACT

Benzimidazoles of the formula

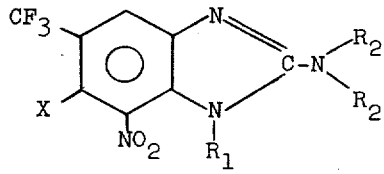

wherein $R_1$ represents hydrogen or an alkyl group which may optionally be substituted, $R_2$ represents lower alkyl, and X is hydrogen, lower alkoxy or halo. The compounds are useful as intermediates for preparation of herbicides.

8 Claims, No Drawings

2-DIALKYLAMINO-5-TRIFLUOROMETHYL-7-NITROBENZIMIDAZOLES

This invention relates to a novel class of substituted benzimidazoles and, more particularly, to a group of 2-dialkylamino-5-trifluoromethyl-7-nitrobenzimidazoles which are useful as intermediates for preparation of herbicides. The novel benzimidazoles of this invention have the formula

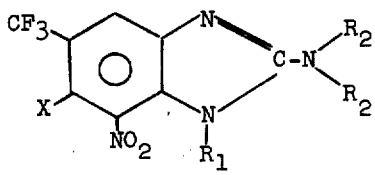

in which $R_1$ represents hydrogen, lower alkyl, halo-substituted lower alkyl, lower cycloalkyl, or lower alkoxy-substituted lower alkyl; $R_2$ represents lower alkyl; and X represents hydrogen, halo or lower alkoxy. For example, X can represent chloro or methoxy.

Thus, the benzimidazoles must have a nitro group at the 7-position and a trifluoromethyl group at the 5-position of the molecule as well as the dialkylamino group at the 2-position. Other possible substituents which are at the 6-position, represented by X in the above formula, include the halogens, such as bromo, chloro, iodo and fluoro, and lower alkoxy of 1 to about 6 carbon atoms such as methoxy, ethoxy, n-butoxy, and n-hexyloxy. Benzimidazoles having no substituent at the 1-position can occur in two tautomeric forms and can be named, for example, 7(4)-nitro-5-(6)-trifluoromethylbenzimidazoles. Both forms are meant to be included within the scope of the specification and claims.

$R_1$ and $R_2$ can each represent a lower alkyl group and may contain from 1 to about 6 carbon atoms, as for example, methyl, ethyl, n-propyl, isopropyl, sec-butyl, 3-pentyl, n-hexyl, and the like. Both $R_2$'s may represent methyl, for example. The alkyl groups represented by $R_1$ can be cyclic or may also have halo substituents, such as bromo, fluoro and chloro, and lower alkoxy substituents, such as defined above. Examples of such groups include chloroethyl, bromoethyl, difluoroethyl, 3-bromopropyl, cyclohexyl, cyclobutyl, methoxymethyl, 2,2-diethoxyethyl, 1-methyl-2-methoxyethyl, 2-methoxypropyl, dichloromethyl, cyclopropyl, chloromethyl and 3-chloropropyl.

Representative compounds, according to the present invention include:

7-nitro-2-dimethylamino-6-chloro-5-trifluoromethylbenzimidazole
7-nitro-1-sec-butyl-2-diethylamino-6-chloro-5-trifluoromethylbenzimidazole
7-nitro-2-diethylamino-6-bromo-5-trifluoromethylbenzimidazole
7-nitro-1-ethyl-6-methoxy-2-dimethylamino-5-trifluoromethylbenzimidazole
7-nitro-6-fluoro-1-methyl-2-dimethylamino-5-trifluoromethylbenzimidazole
7-nitro-6-chloro-1-cyclopropyl-2-dimethylamino-5-trifluoromethylbenzimidazole
7-nitro-6-bromo-2-di-n-propylamino-5-trifluoromethylbenzimidazole
7-nitro-2-dimethylamino-1-isopropyl-6-methoxy-5-trifluoromethylbenzimidazole
7-nitro-2-ethylmethylamino-1-ethyl-6-chloro-5-trifluoromethylbenzimidazole
7-nitro-6-chloro-2-dimethylamino-1-(2-chloroethyl)-5-trifluoromethylbenzimidazole
7-nitro-1-(1-methyl-2-methoxyethyl)-2-dimethylamino-6-bromo-5-trifluoromethylbenzimidazole
7-nitro-6-ethoxy-2-diethylamino-5-trifluoromethylbenzimidazole The compounds of this invention are generally crystalline solids, being soluble in organic solvents such as alcohol, acetone, the chlorinated hydrocarbons, benzene, etc. They are readily prepared by reaction of the corresponding substituted o-phenylenediamine with a phosgeneimmonium chloride [N-(dichloromethylene)-N,N-dialkylammonium chloride] according to the following equation.

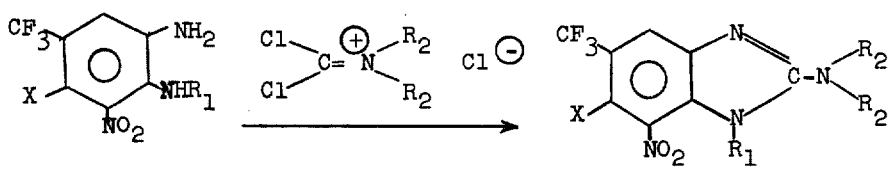

wherein $R_1$, $R_2$ and X have the significance previously assigned.

In some cases, such as when the 6-position is substituted, it may be more convenient to prepare the benzimidazole free of a 7-substituent and then add the nitro group, such as by reaction with nitric acid or other suitable nitrating agents. A suitable synthesis is illustrated as follows.

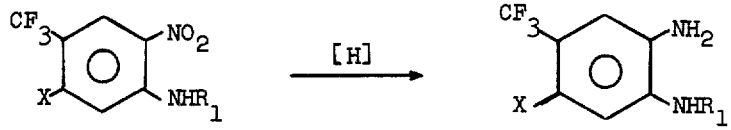

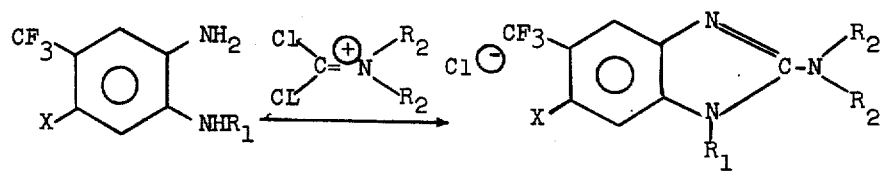

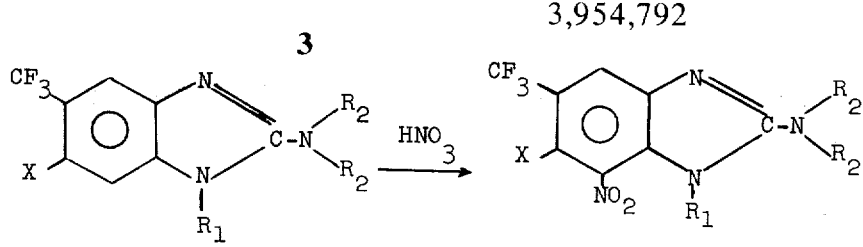

Thus, the method for preparing the compounds of this invention can be generically described as comprising the reaction of an o-phenylenediamine of the formula

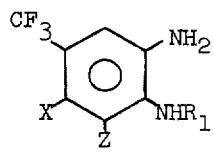

with an N-(dichloromethylene)-N,N-dialkylammonium chloride (also known as N,N-dialkylphosgeneimmonium chloride) of the formula

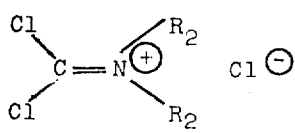

wherein Z is selected from hydrogen and nitro, with the proviso that when Z is hydrogen, the resultant benzimidazole product unsubstituted at the 7-position) is further reacted with a nitrating agent to produce the 7-nitrobenzimidazole. Well-known nitrating agents, such as nitric acid-sulfuric acid mixtures, can be used. Generally, it is preferred that the benzimidazole contain a 6-substituent when the 7-nitrobenzimidazole is produced by nitration as the last step of the process.

See British Patent 1,298,020 which describes preparation of 2,6-dinitro-3-halo-4-trifluoromethylanilines by reaction of a 2,4-dihalo-3,5-dinitrobenzotrifluoride with an amine, and U.S. Pat. No. 3,617,250 which shows preparation of 3-halo-6-nitro-4-trifluoromethylanilines by reaction of two moles of amine with one mole of 2,4-dihalo-5-nitrobenzotrifluoride. The halo group can be replaced by an alkoxy group by known procedures, if desired. See also U.S. Pat. No. 3,466,329 which shows the chemical reduction of 2,6-dinitro-4-trifluoromethylanilines employing sodium sulfide to produce the corresponding 6-nitro-4-trifluoromethyl-1,2-phenylenediamine.

The following examples illustrate the preparation of representative compounds of this invention.

EXAMPLE I

7-Nitro-6-chloro-2-(dimethylamino)-1-ethyl-5-trifluoromethylbenzimidazole

To a solution of 2.86 g. of 4-chloro-$N^2$-ethyl-3-nitro-5-trifluoromethyl-1,2-phenylenediamine in 120 ml. of chloroform was added, slowly, 2.50 g. of N,N-dimethylphosgeneimmonium chloride with stirring. After the addition was completed, the resultant mixture was refluxed for 3 days and then poured into an ice-water mixture. After neutralization with sodium hydroxide, the organic phase was separated, dried and evaporated to dryness. The solid residue was washed with n-hexane-ether mixture to leave 1.0 g. of the desired yellow crystalline nitrobenzimidazole, m.p. 121° – 122°C.

EXAMPLE II

7-Nitro-6-chloro-2-(dimethylamino)-1-isopropyl-5-trifluoromethylbenzimidazole $N^2$-isopropyl-4-chloro-5-trifluoromethyl-3-nitro-1,2-phenylenediamine (5.64 g.; 0.02 mole) was dissolved in about 120 ml. of dry chloroform. To this solution was added 4.0 g. of N,N-dimethylphosgene immonium chloride. The resultant mixture was heated at reflux temperature for 48 hours and then poured into ice-water. The water mixture was neutralized with sodium bicarbonate and the resultant organic phase separated and dried over magnesium sulfate. The solvent was removed by evaporation to give a red oily material. Column chromatography through alumina using dichloroethane as eluent gave (1) light red (predominant), (2) light yellow and (3) violet colored fractions. The first two fractions were combined, evaporated, and then recrystallized from ether-hexane to give 4 g. of yellow solid melting at 103° – 104°C.

The compounds of the present invention are useful as intermediates for preparing herbicidal 7-amino-5-trifluoromethylbenzimidazole by reaction with hydrogen in the presence of a catalyst such as platinum oxide according to the following equation:

The following example illustrates the conversion of the present compounds to the corresponding 7-amino benzimidazoles.

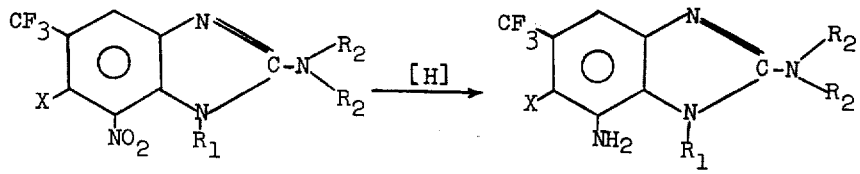

EXAMPLE III

7-Amino-6-chloro-2-dimethylamino-1-ethyl-5-trifluoromethylbenzimidazole 7-nitro-6-chloro-2-dimethylamino-1-ethyl-5-trifluoromethylbenzimidazole (2 g.) in 50 ml. of a 50:50 mixture of dimethoxyethane and methanol was hydrogenated in the presence of 100 mg. of platinum oxide catalyst at an initial pressure of 40 psi. for 3 hours. Filtration to remove the catalyst was followed by solvent removal by evaporation under reduced pressure. The residue was passed through a silica gel column with chloroform as eluent to give 1.1 g. of the desired product melting at 99° – 100°C.

The 7-amino benzimidazoles are useful as herbicides as described in copending applications of Don L. Hunter et al., Ser. No. 476,012 and Ser. No. 476,018, both filed June 3, 1974.

Various changes and modifications of the invention can be made, and, to the extent that such variations incorporate the spirit of this invention, they are intended to be included within the scope of the appended claims.

What is claimed is:

1. A compound of the formula

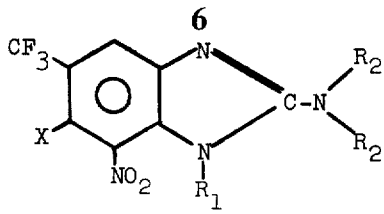

in which $R_1$ represents hydrogen, lower alkyl, halo-substituted lower alkyl, lower cycloalkyl, or lower alkoxy-substituted lower alkyl; $R_2$ represents lower alkyl, and X represents halo or lower alkoxy.

2. A compound in accordance with claim 1 in which said $R_1$ is lower alkyl.
3. A compound in accordance with claim 1 in which said X is chloro.
4. A compound in accordance with claim 1 in which said X is methoxy.
5. A compound in accordance with claim 1 in which said $R_1$ is ethyl.
6. A compound in accordance with claim 1 in which both of said $R_2$'s are methyl.
7. 7-Nitro-6-chloro-2-(dimethylamino)-1-ethyl-5-trifluoromethylbenzimidazole.
8. 7-Nitro-6-chloro-2-(dimethylamino)-1-isopropyl-5-trifluoromethylbenzimidazole.

* * * * *